US00PP15254P2

(12) United States Plant Patent
Stemkens

(10) Patent No.: US PP15,254 P2
(45) Date of Patent: Oct. 19, 2004

(54) ***SUTERA* PLANT NAMED 'SUTHARIS'**

(50) Latin Name: *Sutera diffusa*
Varietal Denomination: Sutharis

(75) Inventor: Henricus Stemkens, Hoorn (NL)

(73) Assignee: Syngenta Seeds B.V. (NL)

( * ) Notice: Subject to any disclaimer, the term of this patent is extended or adjusted under 35 U.S.C. 154(b) by 0 days.

(21) Appl. No.: 10/796,685

(22) Filed: Mar. 8, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Edouard G. Lebel

(57) ABSTRACT

A new *Sutera* plant particularly distinguished by its large, lavender, round flower, early flowering, thick stems and large leaves, and a spreading, trailing habit.

1 Drawing Sheet

Latin name of the genus and species of the plant claimed: *Sutera diffusa.*

Varietal denomination: 'Sutharis'.

BACKGROUND OF THE NEW PLANT

The present invention comprises a new distinct cultivar of *Sutera*, botanically known as *Sutera diffusa.* The new cultivar is propagated from cuttings resulting from the cross of 'B21' and 'B23'. 'B21' is a lavenderblue flowering *Sutera* having a spreading, trailing habit. 'B21' is not commercially available and is not known by any synonyms. 'B23' is a white flowering *Sutera* having a larger than normal flower. 'B23' is not commercially available and is not known by any synonyms. Neither 'B21' or 'B23' has been patented. As a result of this cross the present cultivar was created in 2000 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new *Sutera* plant is an annual in most climatical zones in the US, only in zones 9 and 10 it is a perennial plant.

DESCRIPTION OF THE DRAWING

This new *Sutera* is illustrated by the accompanying photographic drawing which shows blooms, buds and foliage of the plant in full color, the color shown being as true as can be reasonably obtained by conventional photographic procedures.

DATA COLLECTION

The following detailed description set forth the distinctive characteristics of this new *Sutera*. The data which defines these characteristics were collected from asexual reproduction carried out in Enkhuizen, Netherlands. The plant history was taken on 15 weeks old plants, blossomed under natural light in a greenhouse. Color readings were taken in the greenhouse under ambient light. Color references are primarily to The R.H.S. Colour Chart of The Royal Horticultural Society of London.

SUMMARY OF THE INVENTION

Plants of the cultivar 'Sutharis' have not been observed under all possible environmental concitions. The phenotype may vary somewhat with variations in environment such as temperature, light intensity and daylength without, however, any variance in genotype.

The following traits have been repeatedly observed and are determined to be the unique characteristics of 'Sutharis'. These characteristics in combination distinguish 'Sutharis' as a new and distinct variety:

1. Large, lavender, round flowers.
2. Early flowering.
3. Thick stems and large leaves.
4. Spreading, trailing habit.

Plants of the new *Sutera* differ from plants of the parent selections in flowercolor as plants of the female parent 'B21' are much darker in color and plants of the male parent 'B23' are white in color. Also the female parent has thin stems and smaller leaves and the male parent is much later to flower.

Plants of the new *Sutera* can be compared to plants of the *Sutera* variety 'Lavender Showers', disclosed in the abandoned, U.S. Plant patent application Ser. No. 09/450, 098. In side by side comparisons conducted in Enkhuizen, The Netherlands, plants of the new *Sutera* differed from plants of the variety 'Lavender Showers' primarily in size of the flowers and in thickness of the stems, as plants of 'Sutharis' have larger flowers and thicker stems.

DESCRIPTION OF THE NEW CULTIVAR

The Plant

Classification:

*Botanical.—Sutera diffusa.*

Parentage:

*Female parent.*—A seedling named 'B21' is one of our seedlings from our B-generation of plants bred in 1999.

*Pollen parent.*—A seedling named 'B23' is one of our seedlings from our B-generation of plants bred in 1999.

Growth habit: Trailing.

Plant height: 10–18 cm.

Spreading area of plant: 38–48 cm.
Growth rate: Rapid growing.
Strength: Good.
Branching habit: Short internodes and on each knot more than two appearing shoots give a plant that is more branched than normal.
Blooming period: From May till November.

The Stem

Diameter: 2–3 mm.
Shape: Cylindrical.
Anthocyan pigmentation: Absent.
Color of the stem: 137C.
Length of internode: 10–30 mm, depending on the light where the plant is propagated.
Pubescence: Sparse.

The Foliage

Phyllotaxis: Opposite.
Shape of blade: Ovate.
Shape of blade base: Acute.
Shape of blade tip: Truncate.
Leaf margin: Dentate.
Venation: Pinnate.
Texture:
*Upper surface.*—Smooth, glabrous.
*Lower surface.*—Pubescent.
Length: 15–25 mm.
Width: 18–26 mm.
Thickness: 1–2 mm.
Depth of incision: 1–2 mm.
Color:
*Upper side.*—147A.
*Lower side.*—147B.
Length of petiole: 2 mm.
Diameter of petiole: 1 mm.
Color of petiole: 137B.
Fragrance: Musk.

The Bud

Pedicel length: 8–20 mm, depending on season.
Size:
*Diameter.*—2 mm.
*Length.*—4–8 mm.
Shape: Obovate.
Color: 147B.
Sepals:
*Colour.*—147B.
*Shape.*—Erect calyx.
*Number.*—5.
*Size.*—2 mm.

The Flower

Direction: Ascending.
Outward curvation of petal: Medium curved.
Diameter: 15–19 mm.
Tube length: 10–16 mm.
Throat diameter, distal end: 2–3 mm.
Tube diameter, proximal end: 1.5–2.5 mm.
Form: Salverform.
Symmetry: Radial symmetric.
Type: Solitary, auxillary.
Color:
*Upper surface.*—85B.
*Lower surface.*—85B.
Corolla tube: Cylindrical.
Overlapping of petals: Separate.
No. of petals: 5.
Shape of the petals: Gamopetalous, grown together at the base of the petal, forming a corolla.
Petal lobe:
*Length.*—4–7 mm.
*Width.*—3–5 mm.
*Shape.*—Spatulate.
*Apex.*—Rounded.
*Margin.*—Entire.
*Texture.*—Smooth.
Shape of sepals: Gamopetalous, grown together at the base of the sepal.
Calyx:
*Length.*—6–8 mm.
*Diameter.*—3 mm.
*Shape.*—Narrow, linear.
*Apex.*—Acute.
*Margin.*—Entire.
Texture of the calyx:
*Upper surface.*—Pubescent.
*Lower surface.*—Pubescent.
Color of the calyx:
*Upper surface.*—137B.
*Lower surface.*—137C.
Anthocyan pigmentation of calyx limb: Absent.
Peduncle:
*Length.*—5 mm.
*Width.*—Less than 1 mm.
*Angle.*—About 60 degree from the stem.
*Texture.*—Smooth.
*Color.*—137B.
Fragrance: No fragrance detected.
Lastingness of flower: Flowers stay open 8–10 days.

Reproductive Organs

Number of reproductive organs: 1 pistil, 4 stamens.
Pollenproduction: Very low.
Stigma color: Light green 138D.
Stamen color: Yellow 13A.
Stamen arrangement: Didynamous.
Stamen type: Basifixed.
Dehiscence of stamens: Extrorse.
Ovary position: Ovary superior, flower hypogynous.
Style shape: Style terete.
Style length: 5 mm.
Pistil length: 8 mm.

Seeds

Only few seeds are formed, almost sterile plant.

Few seeds that occur are light yellow 13 B, small, round, diameter approx. 0.1 mm.

Roots

Type of roots: Fibrous. Roots start to grow at the nodes that contact the soil.
Physiological and ecological characteristics: Good tolerance to heat and cold. High resistance to lice and whitefly.

Propagation

Propagation is done by cuttings.

Tips of stems are used, which take 6 days to initiate roots and 12 days to develop roots.

What is claimed is:

1. A new and distinct variety of *Sutera* plant, substantially as herein illustrated and described, characterized particularly as to novelty by larger lavender flowers than other *Sutera* plants, earlier to flower, by thick stems and large leaves and a growing habit that is spreading and trailing.

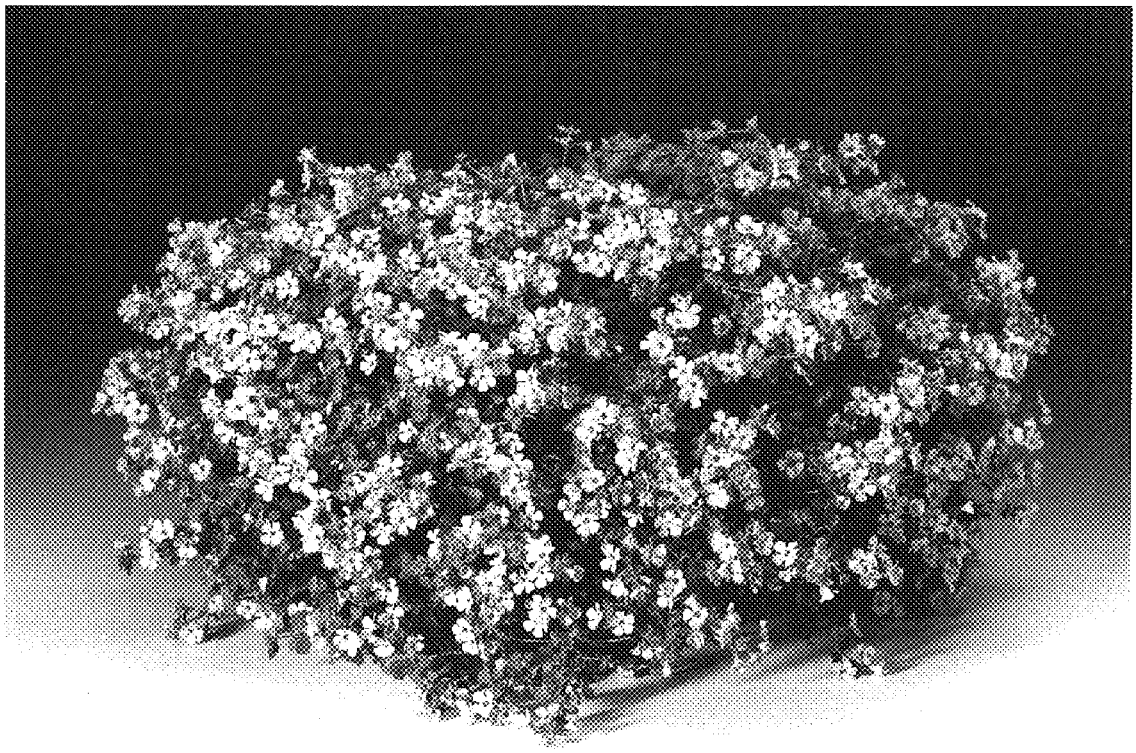

* * * * *